United States Patent [19]
England

[11] 4,206,138
[45] Jun. 3, 1980

[54] PERFLUOROALLYL FLUOROSULFATE AND ITS SULTONE AND POLYMERS
[75] Inventor: David C. England, Wilmington, Del.
[73] Assignee: E. I. Du Pont de Nemours and Company, Wilmington, Del.
[21] Appl. No.: 931,905
[22] Filed: Aug. 8, 1978
[51] Int. Cl.$^2$ .................. C07C 141/02; C07C 141/10
[52] U.S. Cl. ............................. 260/458 F; 526/243; 526/270; 549/89
[58] Field of Search ...................................... 260/458 F
[56] References Cited
U.S. PATENT DOCUMENTS
4,126,631  11/1978  Krespan et al. ................... 260/458 F Primary Examiner—Nicky Chan

[57] ABSTRACT

Hexafluoropropene is reacted with liquid sulfur trioxide in the presence of boric oxide, boron trichloride, boron trifluoride, tri(lower alkyl) borate, boron trioxychloride or boron trioxyfluoride at from 0° C. to 150° C. to form perfluoroallyl fluorosulfate and the sultone thereof. The perfluoroallyl fluorosulfate can be homopolymerized or copolymerized with various fluoroethylenes to form resins useful as ion exchange resins or catalysts. The fluorosulfate groups on the resins can be hydrolyzed to form carboxylic acid groups or various corresponding salts. The sultone of perfluoroallyl fluorosulfate can be rearranged to form β-fluorocarbonyl-β-fluorosulfonyl-trifluorethyl fluorosulfate.

2 Claims, No Drawings

PERFLUOROALLYL FLUOROSULFATE AND ITS SULTONE AND POLYMERS

DESCRIPTION

TECHNICAL FIELD

This invention relates to perfluoroallyl fluorosulfate, to the sultone of perfluoroallyl fluorosulfate, to polymers of perfluoroallyl fluorosulfate, and to β-fluorocarbonyl-β-fluorosulfonyltrifluoroethyl fluorosulfate, the rearranged isomer of the sultone.

BACKGROUND ART

In U.S. Pat. No. 2,852,554, D. C. England discloses the reaction of hexafluoropropene which freshly distilled, liquid, anhydrous sulfur trioxide to obtain 2-hydroxy-1-trifluoromethyl-1,2,2-trifluoroethanesulfonic acid sultone (hexafluoropropene sultone) of the formula

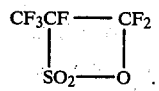

D. C. England, M. A. Dietrich and R. V. Lindsey in "Reaction of Fluoroolefins with SO₃", J. Amer. Chem. Soc., 82, 6181 (1960) also report the reaction of hexafluoropropene (HFP) with freshly distilled sulfur trioxide (SO₃) at 100° C. to give the sultone of HFP

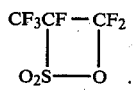

This reference (p. 6184) also reports the reaction of hexafluoropropene with inhibited SO₃ at 60° C. to give an unidentified mixture, bp 50°–65° C. and a high-boiling product which presumably is a cyclic sulfonate-sulfate anhydride of the formula

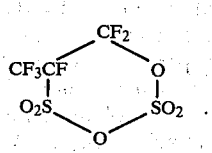

M. A. Belaventsev, L. L. Mikheev, V. M. Pavlov, G. A. Sokol'skii and I. L. Knunyants, Izv. Akad. Nauk SSSR, Ser. Khim. 1972 (11), 2510–16 (Russ), Eng. Trans. p 2441–2445, disclose the reaction of (CF₃)₂C=CF₂ with SO₃ at 150°–180° C. to give

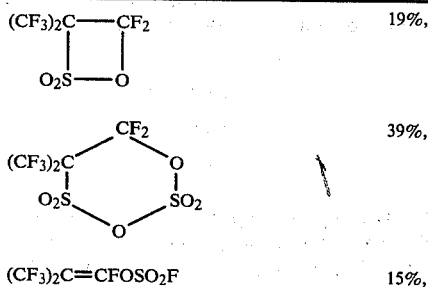

| and | $(CF_3)_2C=CFOSO_3OSO_2F$ | 24%. |

G. A. Sokol'skii, M. A. Belaventsev, and I. L. Knunyants, Izv. Akad, Nauk SSSR, Ser. Khim. 1967 (9) 2020–2024 (Russ), Eng. Trans. p 1935–1938, describe the reaction of the sultone of HFP with NOCl.

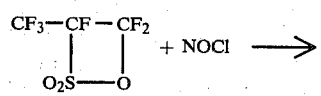

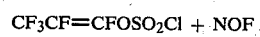

$CF_3CF=CFOSO_2Cl + NOF$

DISCLOSURE OF INVENTION

The present invention relates to the pure compounds, perfluoroallyl fluorosulfate ($CF_2=CF-CF_2OSO_2F$), and its sultone

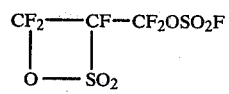

These compounds have not previously been isolated or identified from reactions of HFP and SO₃.

These compounds are readily prepared by reacting hexafluoropropylene ($CF_3-CF=CF_2$) with sulfur trioxide (SO₃) under anhydrous conditions in the presence of about 0.1 to about 5% by weight, based on the sulfur trioxide, of a trivalent boron compound selected from the group consisting of boric oxide (B₂O₃); boron trichloride (BCl₃); boron trifluoride (BF₃); tri(lower alkyl) borates (B(OR)₃) where the alkyl groups contain 1 to 6 carbons, for example, trimethyl borate and triethyl borate; boron trioxychloride ((BOCl)₃); and boron trioxyfluoride ((BOF)₃) at a temperature of about 0° to about 100° C. for a time sufficient to produce perfluoroallyl fluorosulfate.

The sulfur trioxide used in this process can be commercial, liquid sulfur trioxide, or it can be freshly distilled, uninhibited sulfur trioxide. Commercial, liquid sulfur trioxide (mp ~17° C.) is sold in sealed glass ampoules and contains a "stabilizer" which inhibits formation of solid, polymeric sulfur trioxide. Although this material contains a mixture of oligomers (mostly γ-SO₃, the cyclic trimer), it remains liquid. In the absence of inhibitor long chain polymer (solid matter) is formed, but this can be cracked back to liquid form, for example, by heating at 60° C. Water promotes the formation of solid polymer in the presence of inhibitor. For use in preparing the compounds of this invention the SO₃ should be liquid at 20° C.

The general procedure for preparing the compounds of this invention involves addition of sulfur trioxide to a dry, heavy-walled glass tube or a metal tube having a corrosion-resistant liner such as a nickel alloy or stainless steel. Catalyst is added in the amount of about 0.1 to about 5% by weight relative to the sulfur trioxide (preferably about 0.3 to about 2.8% by weight), and hexafluoropropene is either pressured in or condensed in. The mole ratio of hexafluoropropene to sulfur trioxide can vary widely but is preferably about 1:1 to about 3:1. The reaction vessel is sealed and reaction carried out at temperatures from about 0° to about 100° C. (preferably about 25° to about 75° C.) under autogenous pressure for from about one hour to one week. Inert diluents may be used, but they offer no special advantage. Agitation is desirable but not essential. Protic materials such as water, hydrogen chloride, fluorosulfonic acid, methanol, etc. are deleterious to the reaction and should be avoided. The preferred catalysts are $B_2O_3$, $BF_3$, and $B(OCH_3)_3$ because of their efficiency and availability.

The time of reaction depends inversely on temperature. Although lower temperatures require a greater time for maximum yield, they favor perfluoroallyl lfluorosulfate as product over hexafluorosulfate sultone. Higher temperatures tend to decrease yields of perfluoroallyl fluorosulfate and increase the hexafluoropropene sultone content.

It has also been found that perfluoroallyl fluorosulfate and its sultone can be prepared with some batches of undistilled commercial sulfur trioxide without the addition of a trivalent boron compound. It is believed that the batches of sulfur trioxide which produce this result may contain an inhibitor which acts as a catalyst for this reaction. U.S. Pat. No. 2,458,718 suggests that boron compounds have been used as inhibitors for sulfur trioxide.

BEST MODE

The products of the present invention and their preparation and use are illustrated by the following examples. All temperatures are in degree Celsius.

EXAMPLE 1

Preparation of Perfluoroallyl fluorosulfate and the sultone of perfluoroallyl fluorosulfate A mixture of 10 ml of commercial liquid $SO_3$ containing an unknown inhibitor and 45 g of HFP was sealed in a Carius tube at liquid nitrogen temperature, mixed well at room temperature and heated to 150° for four hours. From two such tubes there was obtained by distillation 26.5 g (23%) of 2-hydroxy-1-trifluoromethyl-1,2,2-trifluoroethanesulfonic acid sultone, bp 45°; 18.5 g (16%) of perfluoroallyl fluorosulfate, bp 59°; and 16.4 g (21%) of the sultone of the latter, bp 104°.

ANALYSIS

For perfluoroallyl fluorosulfate: $CF_2{=}CF{-}CF_2OSO_2F$

IR: 5.55μ (C=C), 6.75μ ($SO_2$).

FMR: 46.1 ppm. (triplet, J=8.5 Hz to doublets, J=1.8 Hz, 1 F), −74.0 ppm. (doublets, J=28.2 Hz, to doublets, J=13.9 Hz, to doublets, J=9.5 Hz, to doublets, J=7.8 Hz, 2 F), −91.2 ppm. (doublet, J=50.0 Hz, to doublets, J=40.5 Hz, to triplets, J=7.8 Hz, 1 F), −104.7 ppm. (doublet, J=119.4 Hz, to doublets, J=50.0 Hz, to doublets, J=28.2 Hz), and −192.4 ppm. (doublet, J=119.4 Hz, to doublets, J=40.5 Hz, to triplets, J=13.9 Hz, to doublets, J=1.8 Hz, 1 F).

For sultone of perfluoroallyl fluorosulfate:

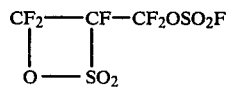

IR: 6.70μ, 6.93μ

FMR: 50.1 ppm. (multiplet, 1 F), −78.0 ppm. (multiplet, 2 F), −81.9 ppm., −83.9 ppm., −88.6 ppm., −90.6 ppm. (AB pattern, 2 F), −152.4 ppm. (multiplet, 1 F).

Anal. Calcd. for $C_3F_6S_2O_6$: C, 11.62; F, 36.77. Found: C, 12.04; F, 37.81.

EXAMPLE 2

Each of four Carius tubes (150 ml capacity) was charged with 10 ml (19 g) of sulfur trioxide (stabilized with dimethyl phthalate) and 12 drops (0.12 g) of trimethyl borate, cooled with liquid nitrogen, necked down and evacuated. Hexafluoropropene (45 g) was condensed into each tube which was then sealed and warmed to melt and mix the contents. They were heated for 14 hrs in a water bath at 55°–60°. Analysis of the product by gas chromatography (gc) indicated that the major product was perfluoroallyl fluorosulfate (FAFS). The combined product of the four tubes was fractionally distilled to give 45 g, b.p. mostly 45°, analyzing by gc 75% 2-hydroxy-1-trifluoromethyl-1,2,2-trifluoroethanesulfonic acid sultone (HFPS) and 25% FAFS; 80 g, b.p. mostly 62°, analyzing by gc 95% FAFS; and 44 g of high-boiler not characterized.

EXAMPLE 3

A 1200-ml Hastalloy tube charged with 167 g (2.09 mol) of distilled $SO_3$, 2 g of boron trifluoride, and 525 g (3.5 mol) of hexafluoropropene was agitated at 25° for 5 days, then at 60° for 8 hr, and at 100° for 2 hr. The tube was cooled to 0°, gases were vented, and the reaction mixture was fractionated to afford 21.9 g (5%) of crude hexafluoropropene sultone, bp 30°–61°, and 288.0 g (60%) of perfluoroallyl fluorosulfate, bp 61°–63°. The perfluoroallyl fluorosulfate was identified by comparison of its IR spectrum with that of the corresponding product of Example 1.

INDUSTRIAL APPLICABILITY

The perfluoroallyl fluorosulfate of the present invention can be homopolymerized or copolymerized with various fluoroethylenes such as vinylidene fluoride, vinyl fluoride, trifluoroethylene, chlorotrifluoroethylene, and tetrafluoroethylene. Particularly preferred copolymers are those of vinylidene fluoride and perfluoroallylfluorosulfate. Generally the copolymer will contain from about 1 to about 80 and preferably about 5 to about 50 weight percent of the perfluoroallylfluorosulfate with a fluoroethylene comprising the remainder of the copolymer. The polymers find use as ion exchange resins and as acid catalysts. Aside from the sulfate group the polymers of the present invention are very temperature stable and chemically inert and, thus, do not interfere in the reaction catalyzed. They permit the use of corrosive or reactive reagents and furthermore permit the operation of the acid catalyzed reaction at high temperatures. Hydrolysis of the perfluoroallyl fluorosulfate polymer results in the formation of carboxylic acid groups. Thus, the polymer will contain repeating units of the structure

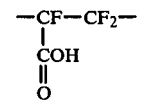

The advantage of this resin over mineral acid is the ready separation of the reaction products from the catalyst, the ability to regenerate the catalyst, the absence of mineral acid waste, and the noncorrosiveness of the catalyst.

The sultone of perfluoroallyl fluorosulfate can be rearranged to form β-fluorocarbonyl-β-fluorosulfonyl-trifluoroethyl fluorosulfate on standing. This triacid fluoride product finds use as a catalyst for polymerizing tetrahydrofuran.

The sultone of perfluoroallyl fluorosulfate can also be reacted with water to form trifluorovinylsulfonyl fluoride which is useful for preparing ion exchange resins and acid catalysts as described by H. H. Gibbs and R. N. Griffin in U.S. Pat. Nos. 3,041,317 and 3,624,053. The sultone can also be reacted with lower alkanols containing 1 to 8 carbon atoms to form dialkylfluorosulfonyl-fluoromalonates. Generally the reaction is carried out at from 0° C. to 60° C. using atmospheric pressure.

EXAMPLE 4

Copolymerization of Perfluoroallyl Fluorosulfate with Vinylidene Fluoride

A mixture of 11 g of perfluoroallyl fluorosulfate, 6.5 g of vinylidene fluoride and 50 microliters of a catalyst solution containing ca. 6% perfluoropropionylperoxide in 1,1,2 -trichloro-1,2,2-trifluoroethane was sealed in a glass tube and rotated at room temperature for five days. When cooled, opened, and low-boiler removed, there was recovered 9.8 g of an elastomer which was soluble in acetone and also in dimethylformamide. Transparent films could be cast from acetone solution or pressed from the solid polymer. Their infrared absorption showed the presence of fluorosulfate (—O-SO$_2$F) groups.

EXAMPLE 5

Copolymerization of Perfluoroallyl Fluorosulfate with Vinylidene Fluoride

In an experiment like the one above, but using 5.5 g of perfluoroallyl fluorosulfate, 5.5 g of vinylidene fluoride and 50 microliters of the catalyst-solution, there was obtained 10.5 g of polymer in 60 hrs.

EXAMPLE 6

Copolymerization of Perfluoroallyl Fluorosulfate with Tetrafluoroethylene

A mixture of 11 g of perfluoroallyl fluorosulfate, 9 g of tetrafluoroethylene and 50 microliters of the catalyst solution sealed in a glass tube for 16 hours at room temperature gave 4 g of the copolymer of tetrafluoro-ethylene and perfluoroallyl fluorosulfate and 13.5 g of volatiles.

EXAMPLE 7

Copolymerization of Perfluoroallyl Fluorosulfate with Vinyl Fluoride

A mixture of 11 g of perfluoroallyl fluorosulfate, 4.5 g of vinyl fluoride and 50 microliters of the catalyst solution sealed in a glass tube at room temperature gave 5.2 g of a dark copolymer of perfluoroallyl fluorosulfate and vinyl fluoride and 4 g of volatile material.

EXAMPLE 8

Rearrangement of the Sultone of Perfluoroallyl Fluorosulfate to β-Fluorocarbonyl-β-fluorosulfonyltrifluoroethyl

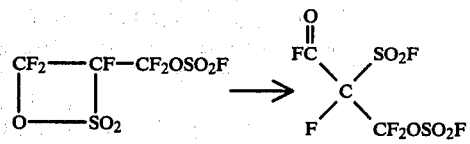

A sample of the above sultone which had been standing for several months in a glass bottle was redistilled. After distilling recovered sultone (b.p. 67° 110 mm), there was distilled the rearranged product, β-fluorocarbonyl-β-fluorosulfonyltrifluoroethyl fluorosulfate, b.p. 84°/30 mm.

ANALYSIS

FMR: 51.7 ppm. (doublet, J=5.2 Hz, 1 F), 50.6 ppm. (triplet, J=8.2 Hz, 1 F), 33.0 ppm. (doublet, J=22.5 Hz, to triplet, J=7.8 Hz, 1 F), −75.5 ppm. (doublet, J=8.2 Hz, to doublet, J=7.8 Hz, to doublet, J=7.5 Hz, 2 F), −155.7 ppm. (doublet, J−J=22.5 Hz to triplet, J=7.5 Hz, to doublet, J=5.2 Hz, 1 F).

EXAMPLE 9

Reaction of the Sultone of Perfluoroallyl Fluorosulfate with Water to form Trifluorovinylsulfonyl Fluoride

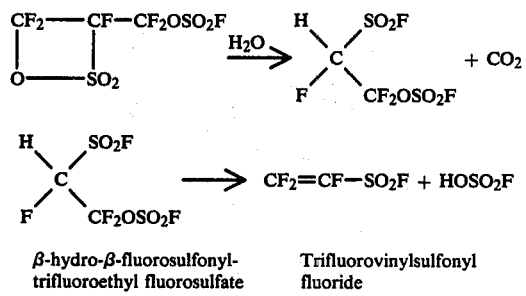

β-hydro-β-fluorosulfonyl-trifluoroethyl fluorosulfate          Trifluorovinylsulfonyl fluoride The above sultone (62 g, 0.2 m) was stirred with cooling to keep the temperature in the range of −10° to +20° C. while adding dropwise 14.4 ml of H$_2$O. The mixture was heated under vacuum and the product was condensed in a dry ice trap. Material in the trap was distilled to give 16 g (46%) of trifluorovinylsulfonyl fluoride, b.p. 53°, and 9.6 g (18%) of β-hydro-β-fluorosulfonyltrifluoroethylfluorosulfate, b.p. 74°/70 mm.

ANALYSIS

For β-hydro-β-fluorosulfonyltrifluoroethylfluorosulfate

IR: 6.70, 6.86 (SO$_2$).

PMR: 5.64 ppm. (doublet J=44.5 Hz to triplets, J=6.1 Hz to doublet, J=2.5 Hz, 1 H).

FMR: 49.1 ppm. (triplet, J=8.4 Hz to doublet, J=1.0 Hz, 1 F), 52.6 ppm. (triplet, J=9.7 Hz, to doublet, J=6.7 Hz, to doublet, J=2.5 Hz, 1 F), −77.9 ppm. (multiplet, 2 F) and −190.5 ppm. (doublet, J=44.5 Hz, to triplet, J=12.3 Hz, to doublets, J=6.7 Hz, to doublets, J=1.0 Hz, 1 F).

Anal. Calcd. for $C_2HF_5S_2O_5$: C, 9.10; H, 0.38; F, 35.98; S, 24.29. Found: C, 9.30; H, 0.40; F, 35.94; S, 25.20.

For trifluorovinylsulfonyl fluoride

IR: 5.70μ (C=C), 6.80μ (SO$_2$).

FMR: 61.2 ppm. (doublet, J=13.8 Hz, to doublet, J=5.3 Hz to doublet, J=4.1 Hz, 1 F), −88.5 ppm. (doublet, J=43.0 Hz, to doublet, J=17.0 Hz, to doublet, J=13.8 Hz, 1 F), −90.9 ppm. (doublet, J=121.8 Hz, to doublet, J=17.0 Hz, to doublet, J=4.1 Hz, 1 F) and −180.9 ppm. (doublet, J=121.8 Hz, to doublet, J=43.0 Hz, to doublet, J=5.3 Hz, 1 F).

Anal. Calcd. for $C_2F_4SO_2$: C, 14.65; F, 46.34; S, 19.55. Found: C, 14.60; F, 45.91; S, 17.29.

I claim:

1. A composition of matter consisting essentially of $CF_2=CFCF_2OSO_2F$.

2. The compound of the formula

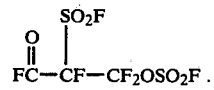

* * * * *